United States Patent
Smiley et al.

(10) Patent No.: US 10,299,913 B2
(45) Date of Patent: May 28, 2019

(54) ACCOMMODATING INTRAOCULAR LENSES AND METHODS OF USE

(71) Applicant: PowerVision, Inc., Belmont, CA (US)

(72) Inventors: Terah Whiting Smiley, San Francisco, CA (US); Daniel Hildebrand, San Francisco, CA (US); Bryan Patrick Flaherty, Half Moon Bay, CA (US)

(73) Assignee: PowerVision, Inc., Belmont, CA (US)

( * ) Notice: Subject to any disclaimer, the term of this patent is extended or adjusted under 35 U.S.C. 154(b) by 180 days.

(21) Appl. No.: 13/672,608

(22) Filed: Nov. 8, 2012

(65) Prior Publication Data

US 2013/0131794 A1 May 23, 2013

Related U.S. Application Data

(60) Provisional application No. 61/557,237, filed on Nov. 8, 2011.

(51) Int. Cl.
*A61F 2/16* (2006.01)

(52) U.S. Cl.
CPC .......... *A61F 2/1635* (2013.01); *A61F 2/1613* (2013.01); *A61F 2/1616* (2013.01); *A61F 2/1624* (2013.01); *A61F 2/1648* (2013.01); *A61F 2002/169* (2015.04); *A61F 2002/1682* (2015.04); *A61F 2002/1683* (2013.01); *A61F 2210/0061* (2013.01); *A61F 2210/0066* (2013.01); *A61F 2250/0018* (2013.01)

(58) Field of Classification Search
CPC .... A61F 2/1613; A61F 2/1635; A61F 2/1648; A61F 2/16; A61F 2250/0053; A61F 2/1616; A61F 2/1629; A61F 2/1618; A61F 2002/1681; A61F 2250/0008; A61F 2250/0009; A61F 2250/001; A61F 2250/0018; A61F 2250/0036; A61F 2002/1683–2002/1686
USPC ......... 623/6.13, 6.15, 6.22, 6.28, 6.27, 6.37, 623/6.38, 6.49
See application file for complete search history.

(56) References Cited

U.S. PATENT DOCUMENTS

| | | |
|---|---|---|
| 4,111,995 A | 9/1978 | Nelson |
| 4,251,887 A | 2/1981 | Anis |
| 4,253,199 A | 3/1981 | Banko |
| 4,254,509 A | 3/1981 | Tennant |

(Continued)

FOREIGN PATENT DOCUMENTS

| | | |
|---|---|---|
| CN | 1283974 A | 2/2001 |
| CN | 1367667 A | 9/2002 |

(Continued)

OTHER PUBLICATIONS

Baughman et al., "Negative poisson's ratios for extreme states of matter," Science, vol. 288, pp. 2018-2022, Jun. 16, 2000.

(Continued)

*Primary Examiner* — Paul B Prebilic
(74) *Attorney, Agent, or Firm* — S. Brannon Latimer

(57) ABSTRACT

Accommodating intraocular lenses and methods of use. The accommodating intraocular lenses include peripheral regions that are adapted to be more responsive to certain types of forces than to other types of forces. For example, the accommodating intraocular lenses can include haptics that are stiffer in an anterior-to-posterior direction than in a radial direction.

7 Claims, 9 Drawing Sheets

(56) References Cited

U.S. PATENT DOCUMENTS

| | | | |
|---|---|---|---|
| 4,304,895 A | 12/1981 | Loshaek | |
| 4,373,218 A | 2/1983 | Schachar | |
| 4,409,691 A | 10/1983 | Levy | |
| 4,423,809 A | 1/1984 | Mazzocco | |
| 4,435,855 A * | 3/1984 | Pannu | A61F 2/16 33/512 |
| 4,435,856 A | 3/1984 | L'Esperance | |
| 4,466,705 A | 8/1984 | Michelson | |
| 4,490,860 A | 1/1985 | Rainin | |
| 4,494,254 A | 1/1985 | Lopez | |
| 4,512,040 A | 4/1985 | McClure | |
| 4,528,311 A | 7/1985 | Beard et al. | |
| 4,575,373 A | 3/1986 | Johnson | |
| 4,585,457 A | 4/1986 | Kalb | |
| 4,604,295 A | 8/1986 | Humphreys | |
| 4,615,701 A | 10/1986 | Woods | |
| 4,620,954 A | 11/1986 | Singer et al. | |
| 4,685,921 A | 8/1987 | Peyman | |
| 4,685,922 A | 8/1987 | Peyman | |
| 4,693,717 A | 9/1987 | Michelson | |
| 4,720,286 A | 1/1988 | Bailey et al. | |
| 4,731,078 A | 3/1988 | Stoy et al. | |
| 4,731,079 A | 3/1988 | Stoy | |
| 4,731,080 A | 3/1988 | Galin | |
| 4,764,423 A | 8/1988 | Yamaguchi et al. | |
| 4,784,485 A | 11/1988 | Ho | |
| 4,787,903 A | 11/1988 | Grendahl | |
| 4,790,847 A | 12/1988 | Woods | |
| 4,813,956 A | 3/1989 | Gupta | |
| 4,816,031 A | 3/1989 | Pfoff | |
| 4,836,201 A | 6/1989 | Patton et al. | |
| 4,842,601 A | 6/1989 | Smith | |
| 4,848,343 A | 7/1989 | Wallsten et al. | |
| 4,888,012 A | 12/1989 | Horn et al. | |
| 4,892,543 A | 1/1990 | Turley | |
| 4,902,293 A | 2/1990 | Feaster | |
| 4,913,536 A | 4/1990 | Barnea | |
| 4,919,151 A | 4/1990 | Grubbs et al. | |
| 4,932,966 A * | 6/1990 | Christie et al. | 623/6.13 |
| 4,946,469 A | 8/1990 | Sarfarazi | |
| 4,950,289 A | 8/1990 | Krasner | |
| 4,963,148 A | 10/1990 | Sulc et al. | |
| 4,994,082 A | 2/1991 | Richards et al. | |
| 4,995,879 A | 2/1991 | Dougherty | |
| 4,995,880 A | 2/1991 | Galib | |
| 5,015,254 A | 5/1991 | Greite | |
| 5,035,710 A | 7/1991 | Nakada et al. | |
| 5,047,051 A | 9/1991 | Cumming | |
| 5,061,914 A | 10/1991 | Busch et al. | |
| 5,066,301 A | 11/1991 | Wiley | |
| 5,078,740 A | 1/1992 | Walman | |
| 5,145,884 A | 9/1992 | Yamamoto et al. | |
| 5,145,935 A | 9/1992 | Hayashi | |
| 5,152,789 A | 10/1992 | Willis | |
| 5,171,266 A | 12/1992 | Wiley et al. | |
| 5,200,430 A | 4/1993 | Federman | |
| 5,201,763 A | 4/1993 | Brady et al. | |
| 5,203,788 A | 4/1993 | Wiley | |
| 5,213,579 A | 5/1993 | Yamada et al. | |
| 5,224,957 A | 7/1993 | Gasser et al. | |
| 5,235,003 A | 8/1993 | Ward et al. | |
| 5,251,993 A | 10/1993 | Sigourney | |
| 5,275,623 A | 1/1994 | Sarfarazi | |
| 5,275,624 A | 1/1994 | Hara et al. | |
| 5,288,293 A | 2/1994 | O'Donnell, Jr. | |
| 5,290,892 A | 3/1994 | Namdaran et al. | |
| 5,326,347 A * | 7/1994 | Cumming | 623/6.38 |
| 5,391,590 A | 2/1995 | Gerace et al. | |
| 5,405,386 A | 4/1995 | Rheinish et al. | |
| 5,426,166 A * | 6/1995 | Usifer | C08F 290/067 526/301 |
| 5,443,506 A | 8/1995 | Garabet | |
| 5,444,106 A | 8/1995 | Zhou et al. | |
| 5,444,135 A | 8/1995 | Cheradame et al. | |
| 5,476,514 A | 12/1995 | Cumming | |
| 5,489,302 A | 2/1996 | Skottun | |
| 5,496,366 A | 3/1996 | Cumming | |
| 5,506,300 A | 4/1996 | Ward et al. | |
| 5,512,609 A | 4/1996 | Yang | |
| 5,567,365 A * | 10/1996 | Weinschenk, III | A61F 2/1613 264/1.7 |
| 5,578,081 A | 11/1996 | McDonald | |
| 5,585,049 A | 12/1996 | Grisoni et al. | |
| 5,593,436 A | 1/1997 | Langerman | |
| 5,607,472 A | 3/1997 | Thompson | |
| 5,628,795 A | 5/1997 | Langerman | |
| 5,633,504 A | 5/1997 | Collins et al. | |
| 5,665,822 A | 9/1997 | Bitler et al. | |
| 5,674,282 A | 10/1997 | Cumming | |
| 5,676,669 A | 10/1997 | Colvard | |
| 5,693,095 A | 12/1997 | Freeman et al. | |
| 5,697,973 A | 12/1997 | Peyman et al. | |
| 5,702,441 A | 12/1997 | Zhou | |
| 5,774,273 A | 6/1998 | Bornhorst | |
| 5,776,191 A | 7/1998 | Mazzocco | |
| 5,776,192 A | 7/1998 | McDonald | |
| 5,843,188 A | 12/1998 | McDonald | |
| 5,891,931 A | 4/1999 | Leboeuf et al. | |
| 5,928,282 A | 7/1999 | Nigam | |
| 5,964,802 A | 10/1999 | Anello et al. | |
| 5,968,095 A | 10/1999 | Norrby | |
| 5,984,962 A | 11/1999 | Anello et al. | |
| 6,013,101 A | 1/2000 | Israel | |
| 6,015,842 A | 1/2000 | Leboeuf et al. | |
| 6,102,539 A | 8/2000 | Tucker | |
| 6,117,171 A | 9/2000 | Skottun | |
| 6,124,980 A | 9/2000 | Cerbell | |
| 6,139,576 A | 10/2000 | Doyle et al. | |
| 6,160,084 A | 12/2000 | Langer et al. | |
| 6,176,878 B1 | 1/2001 | Gwon et al. | |
| 6,180,687 B1 | 1/2001 | Hammer et al. | |
| 6,188,526 B1 | 2/2001 | Sasaya et al. | |
| 6,190,410 B1 | 2/2001 | Lamielle et al. | |
| 6,195,807 B1 | 3/2001 | Chou | |
| 6,197,059 B1 | 3/2001 | Cumming | |
| 6,217,612 B1 | 4/2001 | Woods | |
| 6,225,367 B1 | 5/2001 | Chaouk et al. | |
| 6,229,641 B1 | 5/2001 | Kosaka | |
| 6,299,641 B1 | 10/2001 | Woods | |
| 6,302,911 B1 | 10/2001 | Hanna | |
| 6,322,589 B1 | 11/2001 | Cumming | |
| 6,342,073 B1 | 1/2002 | Cumming et al. | |
| 6,348,437 B1 | 2/2002 | Avery et al. | |
| 6,387,126 B1 | 5/2002 | Cumming | |
| 6,388,043 B1 | 5/2002 | Langer et al. | |
| 6,406,494 B1 | 6/2002 | Laguette et al. | |
| 6,413,262 B2 | 7/2002 | Saishin et al. | |
| 6,423,094 B1 | 7/2002 | Sarfarazi | |
| 6,436,092 B1 | 8/2002 | Peyman | |
| 6,443,985 B1 | 9/2002 | Woods | |
| 6,450,642 B1 | 9/2002 | Jethmalani et al. | |
| 6,464,725 B2 | 10/2002 | Skottun | |
| 6,488,708 B2 | 12/2002 | Sarfarazi | |
| 6,493,151 B2 | 12/2002 | Schachar | |
| 6,503,276 B2 | 1/2003 | Lang et al. | |
| 6,517,577 B1 | 2/2003 | Callahan et al. | |
| 6,528,602 B1 | 3/2003 | Freeman et al. | |
| 6,551,354 B1 | 4/2003 | Ghazizadeh et al. | |
| 6,552,860 B1 | 4/2003 | Alden | |
| 6,554,859 B1 | 4/2003 | Lang et al. | |
| 6,585,768 B2 | 7/2003 | Hamano et al. | |
| 6,589,550 B1 | 7/2003 | Hodd et al. | |
| 6,592,621 B1 | 7/2003 | Domino | |
| 6,599,317 B1 | 7/2003 | Weinschenk, III et al. | |
| 6,601,956 B1 | 8/2003 | Jean et al. | |
| 6,610,350 B2 | 8/2003 | Suzuki et al. | |
| 6,616,691 B1 | 9/2003 | Tran | |
| 6,616,692 B1 | 9/2003 | Glick et al. | |
| 6,638,304 B2 | 10/2003 | Azar | |
| 6,638,305 B2 | 10/2003 | Laguette | |
| 6,638,306 B2 | 10/2003 | Cumming | |
| 6,645,245 B1 | 11/2003 | Preussner | |
| 6,645,246 B1 | 11/2003 | Weinschenk, III et al. | |
| 6,656,223 B2 | 12/2003 | Brady | |

(56) References Cited

U.S. PATENT DOCUMENTS

| | | |
|---|---|---|
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,041,134 B2 | 5/2006 | Nguyen et al. |
| 7,060,094 B2 | 6/2006 | Shahinpoor et al. |
| 7,068,439 B2 | 6/2006 | Esch et al. |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,168 B2 | 7/2007 | Esch et al. |
| 7,247,689 B2 | 7/2007 | Makker et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,354,451 B2 | 4/2008 | Koch |
| 7,416,300 B2 | 8/2008 | Wei et al. |
| 7,438,723 B2 | 10/2008 | Esch |
| 7,452,378 B2 | 11/2008 | Zadno-Azizi et al. |
| 7,453,646 B2 | 11/2008 | Lo |
| 7,485,144 B2 | 2/2009 | Esch |
| 7,494,505 B2 | 2/2009 | Kappelhof et al. |
| 7,637,947 B2 | 12/2009 | Smith et al. |
| 7,675,686 B2 | 3/2010 | Lo et al. |
| 7,753,953 B1 | 7/2010 | Yee |
| 7,759,408 B2 | 7/2010 | Schorzman et al. |
| 7,763,069 B2 | 7/2010 | Brady et al. |
| 7,776,088 B2 | 8/2010 | Shadduck |
| 7,878,655 B2 | 2/2011 | Salvati et al. |
| 7,971,997 B2 | 7/2011 | Hiramatsu et al. |
| 7,988,290 B2 | 8/2011 | Campbell et al. |
| 7,988,292 B2 | 8/2011 | Neal et al. |
| 7,988,293 B2 | 8/2011 | Raymond et al. |
| 8,048,155 B2 | 11/2011 | Shadduck |
| 8,158,712 B2 | 4/2012 | Your |
| 8,162,927 B2 | 4/2012 | Peyman |
| 8,241,355 B2 | 8/2012 | Brady et al. |
| 8,303,656 B2 | 11/2012 | Shadduck |
| 8,314,927 B2 | 11/2012 | Choi et al. |
| 8,328,869 B2 | 12/2012 | Smiley et al. |
| 8,361,145 B2 | 1/2013 | Scholl et al. |
| 8,377,125 B2 | 2/2013 | Kellan |
| 8,480,734 B2 | 7/2013 | Kellan et al. |
| 8,523,941 B2 | 9/2013 | Ichinohe et al. |
| 8,574,239 B2 | 11/2013 | Ichinehe et al. |
| 8,613,766 B2 | 12/2013 | Richardson et al. |
| 8,632,589 B2 | 1/2014 | Helmy |
| 9,005,282 B2 | 4/2015 | Chang et al. |
| 9,034,035 B2 | 5/2015 | Betser et al. |
| 2001/0001836 A1 | 5/2001 | Cumming |
| 2001/0016771 A1 | 8/2001 | Cumming |
| 2001/0039449 A1 | 11/2001 | Johnson et al. |
| 2001/0051826 A1 | 12/2001 | Bogaert et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1* | 7/2002 | Boehm ............... A61F 2/1629 623/6.37 |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1* | 8/2003 | Shadduck ............... 623/6.41 |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0066489 A1 | 4/2004 | Benedikt et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0169816 A1* | 9/2004 | Esch ............... 351/160 R |
| 2004/0181279 A1 | 9/2004 | Nun |
| 2004/0230203 A1 | 11/2004 | Yaguchi |
| 2005/0021139 A1 | 1/2005 | Shadduck |
| 2005/0090612 A1* | 4/2005 | Soane ............... B29D 11/00134 524/800 |
| 2005/0113911 A1 | 5/2005 | Peyman |
| 2005/0125000 A1 | 6/2005 | Tourrette et al. |
| 2005/0131535 A1 | 6/2005 | Woods |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0041307 A1* | 2/2006 | Esch ............... A61F 2/1613 623/6.13 |
| 2006/0069433 A1 | 3/2006 | Nun |
| 2006/0100701 A1* | 5/2006 | Esch et al. ............... 623/6.13 |

(56) References Cited

U.S. PATENT DOCUMENTS

| | | |
|---|---|---|
| 2006/0100703 A1 | 5/2006 | Evans et al. |
| 2006/0116763 A1 | 6/2006 | Simpson |
| 2006/0134173 A1 | 6/2006 | Liu et al. |
| 2006/0158611 A1 | 7/2006 | Piers et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0241752 A1 | 10/2006 | Israel |
| 2006/0253196 A1 | 11/2006 | Woods |
| 2007/0004886 A1 | 1/2007 | Schorzman et al. |
| 2007/0005136 A1 | 1/2007 | Richardson |
| 2007/0021831 A1 | 1/2007 | Clarke |
| 2007/0027538 A1 | 2/2007 | Aharoni et al. |
| 2007/0050023 A1 | 3/2007 | Bessiere et al. |
| 2007/0078515 A1 | 4/2007 | Brady |
| 2007/0088433 A1* | 4/2007 | Esch et al. .................. 623/6.13 |
| 2007/0100445 A1 | 5/2007 | Shadduck |
| 2007/0118216 A1* | 5/2007 | Pynson ........................ 623/6.34 |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0203578 A1* | 8/2007 | Scholl et al. ................. 623/6.13 |
| 2007/0213817 A1 | 9/2007 | Esch et al. |
| 2007/0244561 A1 | 10/2007 | Ben Nun |
| 2007/0260157 A1 | 11/2007 | Norrby |
| 2008/0004699 A1 | 1/2008 | Ben Nun |
| 2008/0015689 A1 | 1/2008 | Esch et al. |
| 2008/0027537 A1 | 1/2008 | Gerlach et al. |
| 2008/0033449 A1 | 2/2008 | Cole et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0243247 A1 | 10/2008 | Poley et al. |
| 2008/0269887 A1 | 10/2008 | Cumming |
| 2008/0300680 A1 | 12/2008 | Joshua |
| 2008/0306587 A1 | 12/2008 | Your |
| 2009/0005865 A1 | 1/2009 | Smiley et al. |
| 2009/0030425 A1 | 1/2009 | Smiley et al. |
| 2009/0076602 A1 | 3/2009 | Ho et al. |
| 2009/0124773 A1 | 5/2009 | Zhou et al. |
| 2009/0149952 A1 | 6/2009 | Shadduck |
| 2009/0228101 A1 | 9/2009 | Zadno-Azizi |
| 2009/0234449 A1* | 9/2009 | De Juan et al. ............. 623/6.22 |
| 2009/0248154 A1 | 10/2009 | Dell |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0319040 A1 | 12/2009 | Khoury |
| 2010/0016963 A1* | 1/2010 | Park ........................ A61F 2/1635 623/6.32 |
| 2010/0039709 A1 | 2/2010 | Lo |
| 2010/0063588 A1 | 3/2010 | Park |
| 2010/0069522 A1 | 3/2010 | Linhardt et al. |
| 2010/0094412 A1 | 4/2010 | Wensrich |
| 2010/0131058 A1 | 5/2010 | Shadduck |
| 2010/0131061 A1 | 5/2010 | Callahan et al. |
| 2010/0161049 A1 | 6/2010 | Inoue |
| 2010/0179653 A1 | 7/2010 | Argento et al. |
| 2010/0228344 A1 | 9/2010 | Shadduck |
| 2010/0228346 A1 | 9/2010 | Esch |
| 2010/0324671 A1 | 12/2010 | Shadduck |
| 2010/0324672 A1 | 12/2010 | Esch et al. |
| 2011/0052020 A1 | 3/2011 | Hildebrand et al. |
| 2011/0118834 A1 | 5/2011 | Lo et al. |
| 2011/0153015 A1 | 6/2011 | Simonov et al. |
| 2011/0208301 A1 | 8/2011 | Anvar et al. |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2011/0313522 A1 | 12/2011 | Hayes |
| 2011/0313523 A1 | 12/2011 | Hayes |
| 2012/0022547 A1 | 1/2012 | Hildebrand et al. |
| 2012/0078361 A1 | 3/2012 | Shadduck |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0221102 A1 | 8/2012 | Tanaka et al. |
| 2012/0226351 A1 | 9/2012 | Peyman |
| 2012/0245591 A1 | 9/2012 | Matthews |
| 2012/0253458 A1 | 10/2012 | Geraghty et al. |
| 2012/0253459 A1 | 10/2012 | Reich et al. |
| 2012/0303119 A1 | 11/2012 | Callahan et al. |
| 2012/0330415 A1 | 12/2012 | Callahan et al. |
| 2013/0053954 A1 | 2/2013 | Rao et al. |
| 2013/0060331 A1 | 3/2013 | Shadduck |
| 2013/0103146 A1 | 4/2013 | Smiley et al. |
| 2013/0128368 A1 | 5/2013 | Costache et al. |
| 2013/0184816 A1 | 7/2013 | Hayes |
| 2014/0121768 A1 | 5/2014 | Simpson |
| 2014/0142587 A1 | 5/2014 | Walter et al. |
| 2014/0227437 A1 | 8/2014 | DeBoer et al. |
| 2015/0202041 A1* | 7/2015 | Shadduck ............. A61F 2/1613 623/6.13 |
| 2015/0238310 A1* | 8/2015 | Matthews ............. A61F 2/1678 606/107 |
| 2017/0020662 A1 | 1/2017 | Shadduck |
| 2017/0290658 A1 | 10/2017 | Hildebrand et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |

FOREIGN PATENT DOCUMENTS

| | | |
|---|---|---|
| CN | 1378440 A | 11/2002 |
| CN | 1384727 A | 12/2002 |
| CN | 101039635 A | 9/2007 |
| CN | 101277659 A | 10/2008 |
| CN | 102271622 A | 12/2011 |
| CN | 202288610 A | 7/2012 |
| EP | 0898972 A2 | 3/1999 |
| EP | 2060243 A1 | 5/2009 |
| EP | 2192934 B1 | 5/2011 |
| FR | 2784575 | 4/2000 |
| JP | 07-044938 | 5/1995 |
| JP | 8501715 | 2/1996 |
| JP | 8224295 | 9/1996 |
| JP | 9294754 | 11/1997 |
| JP | 10-206609 | 8/1998 |
| JP | 11-47168 A | 2/1999 |
| JP | 11056998 | 3/1999 |
| JP | 11169391 A | 6/1999 |
| JP | 11276509 | 10/1999 |
| JP | 11332903 A | 12/1999 |
| JP | 2001-502592 A | 2/2001 |
| JP | 2003144387 | 5/2003 |
| JP | 2003-524503 A | 8/2003 |
| JP | 2003530978 | 10/2003 |
| JP | 2006341094 | 12/2006 |
| JP | 2007513715 A | 5/2007 |
| JP | 2007518447 A | 7/2007 |
| JP | 2008-534111 A | 8/2008 |
| JP | 2008531069 | 8/2008 |
| JP | 2008307394 A | 12/2008 |
| JP | 200934451 | 2/2009 |
| SU | 1810052 | 4/1993 |
| WO | WO95/02378 A1 | 1/1995 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 A2 | 2/2004 |
| WO | WO 2004/046768 A2 | 6/2004 |
| WO | WO 2004/072689 A2 | 8/2004 |
| WO | WO 2005/018504 A1 | 3/2005 |

(56) References Cited

FOREIGN PATENT DOCUMENTS

| | | |
|---|---|---|
| WO | WO 2005/084588 A1 | 9/2005 |
| WO | WO 2006/004707 A2 | 1/2006 |
| WO | WO 2006/047383 A2 | 5/2006 |
| WO | WO 2006/088440 A1 | 8/2006 |
| WO | WO 2007/005529 A2 | 1/2007 |
| WO | WO2007/005692 A1 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO 2007/138564 A1 | 12/2007 |
| WO | WO 2008/108524 A1 * 9/2008 ........... A61F 2/1635 |
| WO | WO 2009/100322 A2 | 8/2009 |
| WO | WO 2009/154455 A1 | 12/2009 |
| WO | WO 2011/119334 A1 | 9/2011 |
| WO | WO 2012/006186 A2 | 1/2012 |

OTHER PUBLICATIONS

Baughman, "Avoiding the shrink," Nature, vol. 425, pp. 667, Oct. 16, 2003.
Conlisk, A. T. et al; Mass Transfer and Flow in Electrically Charged Micro- and Nano-channels; Analytical Chemistry, vol. 74; iss. 9; pp. 2139-2150; May 2002.
Dubbelman et al.; The Thickness of the Aging Human Lens Obtained from Corrected Scheimpflug Images; Optometry & Vison Science; vo. 78; iss. 6; pp. 411-416; Jun. 2001.
Gorder, P. F.; Electricity can pump medicine in implanted medical devices; Ohio State Research News; 3 pgs.; May 2, 2002 (printed from internet Aug. 19, 2010).
Gordon, "Applications of shape memory polyurethanes," Proceedings of the First Intl Conf. on Shape Memory and Superelastic Tech., Asilomar Conference Center, Pacific Grove, CA, USA, pp. 115-120, Mar. 1994.
Gruber et al.; Exhaustive soxhlet extraction for the complete removal of residual compounds . . . ; Journal of Biomedical Materials Research; vol. 53; No. 5; pp. 445-448; Mar. 2000.
Jeon et al., "Shape memory and nanostructure in poly(norbornyl-POSS) copolymers," Polymer International, vol. 49, pp. 453-457, May 2000.
Kim et al., "Polyurethanes having shape memory effects," Polymer, vol. 37, No. 26, pp. 5781-5793, Dec. 1996.
Lakes et al., "Dramatically stiffer elastic composite materials due to negative stiffness phase?," Journal of the Mechanics and Physics of Solids, vol. 50, pp. 979-1009, May 2002.
Lakes et al., "Extreme damping in composite materials with negative-stiffness inclusions," Nature, vol. 410, pp. 565-567, Mar. 29, 2001.
Lakes et al., "Microbuckling instability in elastomeric cellular sollids," J. Materials Science, vol. 28, pp. 4667-4672, Jan. 1993.
Lakes, "A broader view of membranes," Nature, vol. 414, pp. 503-504, Nov. 29, 2001.
Lakes; Deformations in extreme matter; Science; perspectives; vol. 288; No. 5473; pp. 1976-1977; Jun. 16, 2000.
Lakes, "Extreme damping in compliant composites with a negative-stiffness phase," Philosophical Magazine Letters, vol. 81, No. 2, pp. 95-100, Feb. 2001.
Lakes, "Extreme damping in composite materials with a negative stiffness phase," Physical Review Letters, vol. 86, No. 13, pp. 2897-2900, Mar. 26, 2001.
Lakes, "Negative poisson's ratio materials," Science, vol. 238, pp. 551, Oct. 23, 1987.
Lakes, "No contractile obligations," Nature, vol. 358, pp. 713-714, Dec. 31, 1992.
Langenbucher et al., "Computerized calculation scheme for toric intraocular lenses," Acta Ophthalmologica Scandinavica, vol. 82, No. 3, pp. 270-276, Jun. 2004.
Lendlein et al., "Biodegradable, elastic shape-memory polymers for potential biomedical applications", Science; vol. 296; pp. 1673-1676; May 31, 2002.

Lendlein et al., "Shape-memory polymers," Angew. Chem. Int. Ed.; vol. 41; pp. 2034-2057; Jun. 2002.
Li et al., "Crystallinity and morphology of segmented polyurethanes with different soft-segment length," Journal of Applied Polymer Science, vol. 62, pp. 631-638, Oct. 1996.
Liu et al., "Thermomechanical characterization of a tailored series of shape memory polymers," Journal of Applied Medical Polymers, vol. 6, No. 2, Dec. 2002.
Mather et al., "Strain recovery in POSS hybrid thermoplastics," Polymer Preprints, vol. 41, No. 1, pp. 528-529, Feb. 2000.
Metcalfe et al., "Cold hibernated elastic memory foams for endovascular interventions," Biomaterials, vol. 24, pp. 491-497, Feb. 2003.
Qiao et al.; Bio-inspired accommodating fluidic intraocular lens; Optics Letters; vol. 34; No. 20; pp. 3214-3216; Oct. 15, 2009.
Rosales et al.; Pentacam Scheimpflug QuantitativeImaging of the Crystalline Lens andIntraocular Lens; J. Refractive Surgery; vol. 25; pp. 421-428; May 2009.
Takahashi et al., "Structure and properties of shape-memory polyurethane block copolymers," Journal of Applied Polymer Science, vol. 60, pp. 1061-1069, May 1996.
Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.
Tobushi et al., "Thermomechanical properties of shape memory polymers of polyurethane series and their applications," Journal de Physique IV, Colloque C1, vol. 6, pp. 377-384, Aug. 1996.
Vass et al.; Prediction of pseudophakic capsular bag diameter based on biometric variables; J Cataract Refract Surg.; vol. 25; pp. 1376-1381; Oct. 1999.
Wang et al., "Deformation of extreme viscoelastic metals and composites," Materials Science and Enginerring A, vol. 370, pp. 41-49, Apr. 2004.
Wang et al., "Extreme stiffness systems due to negative stiffness elements," American Journal of Physics, vol. 72, No. 1, pp. 40-50, Jan. 2004.
Wang et al., "Stable extremely-high-damping discrete viscoelastic systems due to native stiffness elements," Applied Physics Letters, vol. 84, No. 22, pp. 4451-4453, May 31, 2004.
Wyant et al; "Basic Wavefront Aberration Theory for Optical Metrology," Applied Optics and Optical Engineering, vol. XI, Aug. 10, 1992: pp. 1, 28-39.
Xu et al., "Making negative poisson's ratio microstructures by soft lithography," Advanced Materials, vol. 11, No. 14, pp. 1186-1189, Jun. 1999.
International Preliminary Report for PCT/US10/020648 dated Jul. 12, 2011; 7 pages.
Hildebrand et al.; U.S. Appl. No. 14/163,794 entitled "Intraocular Lens Delivery Devices and Methods of Use," filed Jan. 24, 2014.
Matthews et al.; U.S. Appl. No. 13/835,876 entitled "Intraocular Lens Delivery Systems and Methods of Use," filed Mar. 15, 2013.
Shadduck, John; U.S. Appl. No. 14/278,249 entitled "Accommodating intraocular lens," filed May 15, 2014.
Hildebrand et al.; U.S. Appl. No. 13/899,376 entitled "Lens Capsule Size Estimation," filed May 21, 2013.
Esch et al.; U.S. Appl. No. 13/909,946 entitled "Accommodating Intraocular Lenses," filed Jun. 4, 2013.
Hildebrand et al., U.S. Appl. No. 14/728,824 entitled "Intraocular lens delivery devices and methods of use," filed Jun. 2, 2015.
Matthews; U.S. Appl. No. 14/776,752 entitled "Intraocular lens storage and loading devices and methods of use," filed Sep. 15, 2015.
Anvar et al.; U.S. Appl. No. 14/555,001 entitled "Fluid for accommodating intraocular lenses," filed Nov. 26, 2014.
Smiley et al.; U.S. Appl. No. 15/345,020 entitled "Accommodating intraocular lenses," filed Nov. 7, 2016.
Matthews et al.; U.S. Appl. No. 15/369,616 entitled "Intraocular lens delivery systems and methods of use," filed Dec. 5, 2016.
Smiley et al.; U.S. Appl. No. 15/457,934 entitled "Lens delivery system," filed Mar. 13, 2017.

* cited by examiner

ACCOMMODATING INTRAOCULAR LENSES AND METHODS OF USE

CROSS-REFERENCE TO RELATED APPLICATIONS

This application claims the benefit of U.S. Provisional Application No. 61/557,237, filed Nov. 8, 2011, which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The crystalline lens is a transparent, biconvex structure in the eye that, along with the cornea, helps to refract light to be focused on the retina. The crystalline lens, by changing shape, functions to change the focal distance of the eye so that it can focus on objects at various distances. This adjustment of the crystalline lens is known as accommodation. The lens capsule is a smooth, transparent membrane that completely surrounds the lens. The lens capsule is elastic and is composed of collagen. The lens is flexible and its curvature is controlled by ciliary muscles through the zonules, which connect the ciliary muscles and the equatorial region of the capsule. At short focal distance the ciliary muscle contracts, the zonules loosen, and the lens thickens, resulting in a rounder shape and thus high refractive power. Changing focus to an object at a greater distance requires the relaxation of the ciliary muscle, which increases the tension on the zonules, flattening the lens and thus increasing the focal distance.

A crystalline lens can be removed and replaced with an artificial lens, generally referred to as an intraocular lens, for a variety of reasons. Some intraocular lenses are used to replace a cataract lens, a clouding that develops in the crystalline lens of the eye, obstructing the passage of light. Intraocular lenses can be characterized as non-accommodating or accommodating. Accommodating intraocular lenses are designed to function similarly to the native crystalline lens and are adapted to change power to provide near and distance vision.

The native crystalline lens is typically removed through a procedure referred to as an extracapsular extraction. The procedure includes making a capsulorhexis, a circular incision made on the anterior side of the capsule, followed by removal of the lens material. The replacement intraocular lens can then be positioned within the capsule through the opening formed by the circular incision.

As is set forth in more detail in U.S. application Ser. No. 12/685,531, filed Jan. 11, 2010, from which this application claims priority, there is patient-to-patient variability in capsular bag size, there are imperfect techniques for measuring capsular sizes, and there are post-implant changes that can occur within the eye or to the accommodating intraocular lens. Accommodating intraocular lenses are desired for which the base state, or base power (which may also be referred to herein as "set-point"), of the accommodating intraocular lens is more predictable after implanting it within an eye, and yet will still accommodate in response to ciliary muscle movement.

SUMMARY OF THE DISCLOSURE

One aspect of the disclosure is an accommodating intraocular lens comprising an optic portion comprising an optic fluid chamber; and a peripheral non-optic portion secured to and extending peripherally from the optic portion, the peripheral non-optic portion comprising a peripheral fluid chamber in fluid communication with the optic fluid chamber, wherein the peripheral non-optic portion is adapted to deform in response to forces on the peripheral non-optic portion due to ciliary muscle movement to thereby move a fluid between the peripheral fluid chamber and the optic fluid chamber to change an optical parameter of the accommodating intraocular lens, wherein the peripheral non-optic portion is adapted to be more sensitive to forces in the radial direction that it is to forces in the anterior-to-posterior direction.

In some embodiments the peripheral non-optic portion is adapted to deform in response to capsular bag forces on the peripheral non-optic portion due to ciliary muscle movement to thereby move a fluid between the peripheral fluid chamber and the optic fluid chamber to change an optical parameter of the accommodating intraocular lens.

In some embodiments the peripheral non-optic portion is adapted to be more sensitive to capsular bag forces in the radial direction than it is to capsular bag forces in the anterior-to-posterior direction.

In some embodiments the peripheral non-optic portion is adapted to deform more in response to forces in the radial direction that it is to forces in the anterior-to-posterior direction.

In some embodiments the peripheral non-optic portion is adapted such that a greater volume of fluid moves between the peripheral fluid chamber and the optic fluid chamber in response to forces on the peripheral non-optic portion in the radial direction that in response to forces on the peripheral non-optic portion in the anterior-to-posterior direction.

In some embodiments the peripheral non-optic portion is stiffer in the anterior-to-posterior direction that it is in the radial direction. The peripheral non-optic portion can comprise a radially outer body portion adapted to be disposed adjacent a radial portion of the capsular bag, and a radially inner body portion that has a radial thickness greater than a radial thickness of the radial outer body portion, wherein in the relative thicknesses adapt the peripheral non-optic portion to be more sensitive to capsular forces in the radial direction than to capsular forces anterior-to-posterior direction.

In some embodiments, in a cross section of the peripheral non-optic portion in a plane that extends in the anterior-to-posterior direction, an outer surface of the peripheral portion has an axis of symmetry, and wherein the peripheral fluid chamber in the cross section is not symmetrical along the axis of symmetry. The outer surface can have a generally oval configuration. In the cross section the peripheral fluid chamber can have a radially inner surface that is more linear than a radially outer surface.

One aspect of the disclosure is an accommodating intraocular lens comprising an optic portion comprising an optic fluid chamber; and a peripheral non-optic portion secured to and extending peripherally from the optic portion, the peripheral non-optic portion comprising a peripheral fluid chamber in fluid communication with the optic fluid chamber, wherein the peripheral non-optic portion is adapted to deform in response to forces on the peripheral non-optic portion due to ciliary muscle movement to thereby move a fluid between the peripheral fluid chamber and the optic fluid chamber to change an optical parameter of the accommodating intraocular lens, and wherein the peripheral non-optic portion has a stiffness in the anterior-to-posterior direction that is different than a stiffness in the radial direction.

In some embodiments the stiffness in the anterior-to-posterior direction is greater than the stiffness in the radial direction.

In some embodiments the peripheral non-optic portion is adapted to deform in response to capsular bag forces on the peripheral non-optic portion due to ciliary muscle movement to thereby move a fluid between the peripheral fluid chamber and the optic fluid chamber to change an optical parameter of the accommodating intraocular lens.

In some embodiments the peripheral non-optic portion is adapted to be more sensitive to forces in the radial direction than it is to forces in the anterior-to-posterior direction.

In some embodiments the peripheral non-optic portion is adapted to deform more in response to forces in the radial direction that it is to forces in the anterior-to-posterior direction.

In some embodiments the peripheral non-optic portion is adapted such that a greater volume of fluid moves between the peripheral fluid chamber and the optic fluid chamber in response to forces on the peripheral non-optic portion in the radial direction that in response to forces on the peripheral non-optic portion in the anterior-to-posterior direction.

One aspect of the disclosure is an accommodating intraocular lens comprising an optic portion comprising an optic fluid chamber; and a peripheral non-optic portion secured to and extending peripherally from the optic portion, the peripheral non-optic portion comprising a peripheral fluid chamber in fluid communication with the optic fluid chamber, wherein the peripheral non-optic portion is adapted to deform in response to forces on the peripheral non-optic portion due to ciliary muscle movement to thereby move a fluid between the peripheral fluid chamber and the optic fluid chamber to change an optical parameter of the accommodating intraocular lens, and wherein a first volume of fluid moved between the peripheral fluid chamber and the optic fluid chamber in response to forces on the peripheral non-optic portion in the anterior-to-posterior direction is less than a second volume of fluid moved between the peripheral fluid chamber and the optic fluid chamber in response to forces on the peripheral non-optic portion in the radial direction.

In some embodiments the peripheral non-optic portion is adapted to deform in response to capsular bag forces on the peripheral non-optic portion due to ciliary muscle movement to thereby move a fluid between the peripheral fluid chamber and the optic fluid chamber to change an optical parameter of the accommodating intraocular lens.

In some embodiments the peripheral non-optic portion is adapted to be more sensitive to capsular bag forces in the radial direction than it is to capsular bag forces in the anterior-to-posterior direction.

In some embodiments the peripheral non-optic portion is adapted to deform more in response to forces in the radial direction that it is to forces in the anterior-to-posterior direction.

In some embodiments the peripheral non-optic portion is stiffer in the anterior-to-posterior direction that it is in the radial direction. The peripheral non-optic portion comprises a radially outer body portion adapted to be disposed adjacent a radial portion of the capsular bag, and a radially inner body portion that has a radial thickness greater than a radial thickness of the radial outer body portion, wherein in the relative thicknesses adapt the peripheral non-optic portion to be more sensitive to capsular forces in the radial direction than to capsular forces anterior-to-posterior direction.

One aspect of the disclosure is an accommodating intraocular lens, comprising an optic portion comprising an optic fluid chamber; and a peripheral non-optic portion secured to and extending peripherally from the optic portion, the peripheral non-optic portion comprising a peripheral fluid chamber in fluid communication with the optic fluid chamber, wherein the peripheral non-optic portion is adapted to deform in response to forces on the peripheral non-optic portion due to ciliary muscle movement to thereby move a fluid between the peripheral fluid chamber and the optic fluid chamber to change an optical parameter of the accommodating intraocular lens, wherein the peripheral non-optic portion is adapted to resist deformation from capsular forces in the anterior-to-posterior direction more than deformation from capsular forces in the radial direction.

One aspect of the disclosure is an accommodating intraocular lens, comprising an optic portion comprising an optic fluid chamber; and a peripheral non-optic portion secured to and extending peripherally from the optic portion, the peripheral non-optic portion comprising a peripheral fluid chamber in fluid communication with the optic fluid chamber, wherein the peripheral non-optic portion is adapted to deform in response to forces on the peripheral non-optic portion due to ciliary muscle movement to thereby move a fluid between the peripheral fluid chamber and the optic fluid chamber to change an optical parameter of the accommodating intraocular lens, wherein the peripheral non-optic portion is adapted to reconfigure the capsule to a configuration in which the capsule extends further in the anterior-to-posterior direction that in a native configuration.

DETAILED DESCRIPTION

Figure 1A:
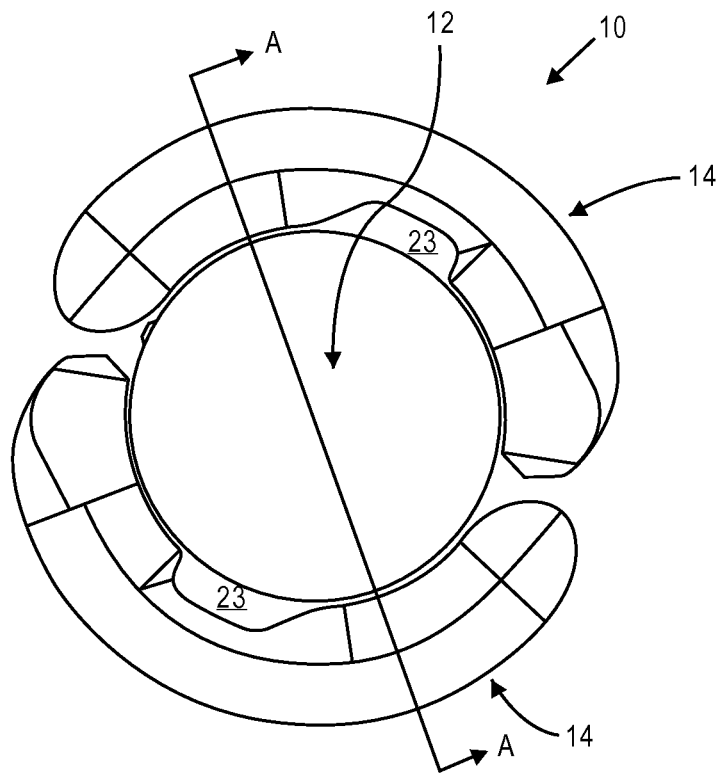
FIGS. 1A and 1B illustrate an exemplary accommodating intraocular lens.

The disclosure relates generally to accommodating intraocular lenses. In some embodiments the accommodating intraocular lenses described herein are adapted to be positioned within a native capsular bag in which a native lens has been removed. In these embodiments a peripheral non-optic portion (i.e., a portion not specifically adapted to focus light on the retina) is adapted to respond to capsular bag reshaping due to ciliary muscle relaxation and contraction. The response is a deformation of the peripheral portion that causes a fluid to be moved between the peripheral portion and an optic portion to change an optical parameter (e.g., power) of the intraocular lens.

The peripheral portions of the accommodating intraocular lenses described herein are adapted so that at least a portion of the peripheral portions is less responsive, or less sensitive, to certain types of capsular forces than to other types of capsular forces. Less responsive, or less-sensitive, as used herein, generally means that the optical power of the accommodating intraocular lens will change less in response to the types of forces to which the peripheral portion is less sensitive than to other types of forces. In general, the peripheral portions are adapted to be less responsive to forces in the anterior-to-posterior direction than to forces in the radial direction. In some cases the forces in the anterior-to-posterior direction are non-ciliary muscle related capsular forces, such as from size mismatch between the capsular bag and the intraocular lens, or from a capsular bag healing response. The radial forces as described herein are capsular reshaping and capsular forces resulting from ciliary muscle contraction and relaxation, causing accommodation of the accommodating intraocular lens. The accommodating intraocular lenses herein are thus considered to be more sensitive to radial forces than to forces in the anterior-to-posterior direction, and thus the optical power of the accommodating intraocular lens will change more in response to the radial forces than it will in response to forces in the anterior-to-posterior direction.

One of the benefits of the peripheral portions described herein is that they reshape the capsule, by essentially "propping" it open, in a predictable way while still preserving the radial sensitivity of the peripheral portion to radial forces to allow the accommodating lens to accommodate. Variations in the base state of the accommodating intraocular lens due to one or more of anatomical variations in capsule size, inaccurate capsule measurements, or post-implant changes in the capsule are reduced because the peripheral portion is adapted to more predictably reshape the capsule in at least one direction. In some embodiments the peripheral portion is adapted to reshape the capsule in a more predictable way because it is stiffer in at least one direction. For example, in some embodiments the peripheral portion is stiffer in the anterior-to-posterior direction than in the radial direction. In these embodiments the peripheral portion is adapted to prop open the capsule in the anterior-to-posterior direction.

As used herein, "anterior-to-posterior," or derivatives thereof, is not intended to be limited to the direction that is perfectly parallel to the optical axis, but is interpreted to mean a direction that is generally in what is typically referred to as the anterior-to-posterior direction. For example without limitation, the "anterior-to-posterior" direction includes directions or axes that are 10 degrees from the optical axis of the accommodating intraocular lens. The "radial" forces described herein are not to be considered to be in the anterior-to-posterior direction.

Figure 1B:
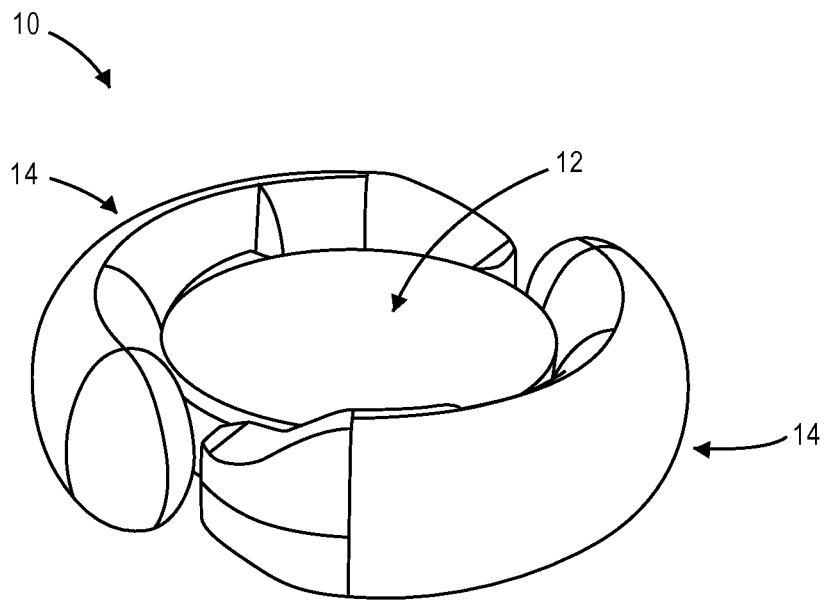

FIG. 1A is a top view illustrating accommodating intraocular lens 10 that includes optic portion 12 and a peripheral portion that in this embodiment includes first and second haptics 14 coupled to and extending peripherally from optic portion 12. Optic portion 12 is adapted to refract light that enters the eye onto the retina. Haptics 14 are configured to engage a capsular bag and are adapted to deform in response to ciliary muscle related capsular bag reshaping. FIG. 1B is a perspective view of intraocular lens 10 showing optic portion 12 and haptics 14 coupled to optic portion 12.

The haptics are in fluid communication with the optic portion. Each haptic has a fluid chamber that is in fluid communication with an optic chamber in the optic portion. The haptics are formed of a deformable material and are adapted to engage the capsular bag and deform in response to ciliary muscle related capsular bag reshaping. When the haptics deform the volume of the haptic fluid chamber changes, causing a fluid disposed in the haptic fluid chambers and the optic fluid chamber to either move into the optic fluid chamber from the haptic fluid chambers, or into the haptic fluid chambers from the optic fluid chamber. When the volume of the haptic fluid chambers decreases, the fluid is moved into the optic fluid chamber. When the volume of the haptic fluid chamber increases, fluid is moved into the haptic fluid chambers from the optic fluid chamber. The fluid flow into and out of the optic fluid chamber changes the configuration of the optic portion and the power of the intraocular lens.

Figure 1C:
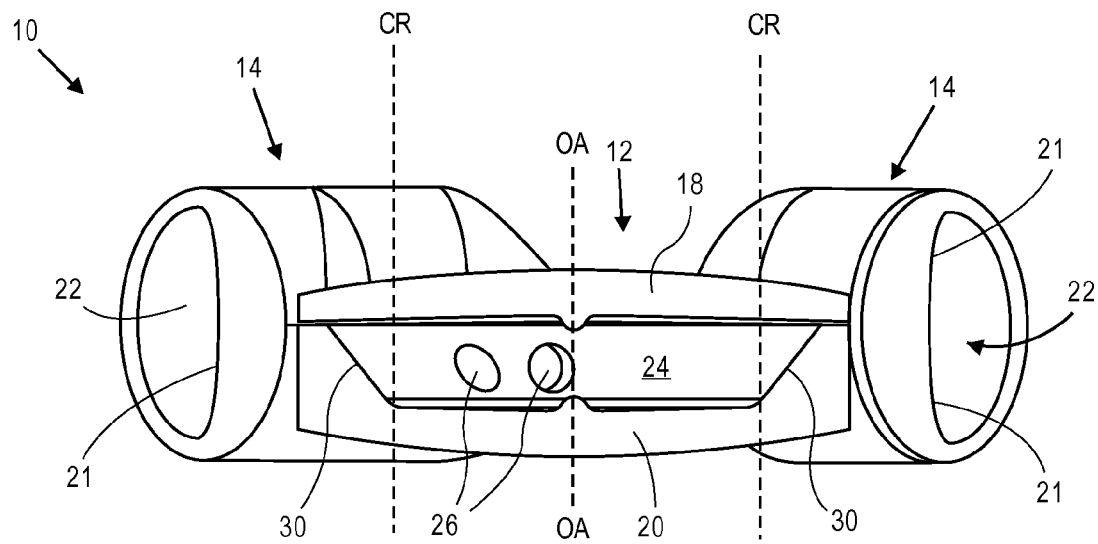
FIG. 1C illustrates a sectional view of the accommodating intraocular lens from FIGS. 1A and 1B.

FIG. 1C is a side sectional view through Section A-A indicated in FIG. 1A. Optic portion 12 includes deformable anterior element 18 secured to deformable posterior element 20. Each haptic 14 includes a fluid chamber 22 that is in fluid communication with optic fluid chamber 24 in optic portion 12. Only the coupling between the haptic 14 to the left in the figure and option portion 12 is shown (although obscured) in the sectional view of FIG. 1C. The haptic fluid chamber 22 to the left in the figure is shown in fluid communication with optic fluid chamber 24 via two apertures 26, which are formed in posterior element 20. The haptic 14 to the right in FIG. 1C is in fluid communication with optic chamber 24 via two additional apertures also formed in posterior element (not shown) substantially 180 degrees from the apertures shown.

Figure 1D:
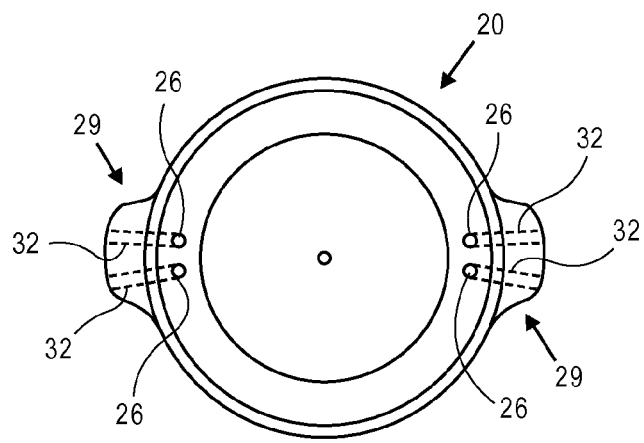
FIG. 1D is a top view of an exemplary posterior element of an accommodating intraocular lens.

FIG. 1D is a top view of posterior element 20 (anterior element 18 and haptics 14 not shown). Posterior element 20 includes buttress portions 29 in which channels 32 are formed. Channels 32 provide fluid communication between optic portion 12 and haptics 14. Apertures 26 are disposed at one end of channels 32. The optic fluid chamber 24 is therefore in fluid communication with a single haptic via two fluid channels. Buttress portions 29 are configured and sized to be disposed within an opening formed in haptics 14 that defines one end of the haptic fluid chamber, as described below. Each of buttress portions 29 includes two channels formed therein. A first channel in a first buttress is in alignment with a first channel in the second buttress. The second channel in the first buttress is in alignment with the second channel in the second buttress.

Figure 1E:
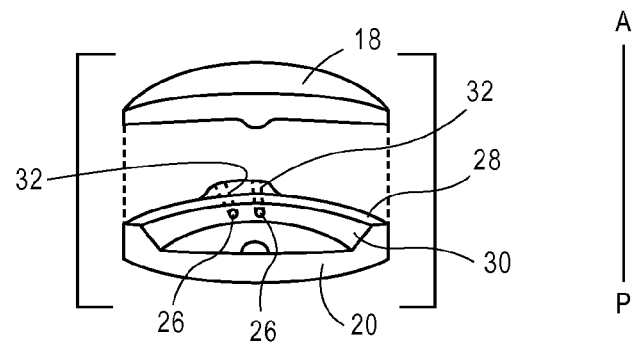
FIG. 1E is a sectional assembly view of an exemplary optic portion of an accommodating intraocular lens.

There are advantages to having two channels in each buttress as opposed to one channel. A design with two channels rather than one channel helps maintain dimensional stability during assembly, which can be important when assembling flexible and thin components. Additionally, it was observed through experimentation that some one-channel designs did not provide adequate optical quality throughout the range of accommodation. In particular, lens astigmatism was observed in some one-channel designs, particularly as the intraocular lens accommodated. It was discovered that the two-channel buttress designs described herein reduced astigmatism, particularly as the lens accommodated. Astigmatism is reduced in these embodiments because the stiffness of the buttress is increased by the rib portion between the two channels. The additional stiffness results in less deflection due to pressure changes in the channels. Less deflection due to the pressure changes in the channels results in less astigmatism. In some embodiments the channels are between about 0.4 mm and about 0.6 mm in diameter. In some embodiments the channels are about 0.5 mm in diameter. In some embodiments the distance between the apertures is about 0.1 mm to about 1.0 mm FIG. 1E is a side assembly view through section A-A of optic portion 12, which includes anterior element 18 and posterior element 20 (haptics not shown for clarity). By including fluid channels 32 in posterior element 20, posterior element 20 needs to have enough structure through which the channels 32 can be formed. Buttress portions 29 provide that structures in which channels 32 can be formed. At its peripheral-most portion posterior element 20 is taller than anterior element 18 in the anterior-to-posterior direction. In alternative embodiments, the channels can be formed in anterior element 18 rather than posterior element 20. The anterior element would include buttress portions 29 or other similar structure to provide structure in which the channels can be formed. In these alternative embodiments the posterior element could be formed similarly to anterior element 18.

As shown in FIG. 1E, posterior element 20 is secured to anterior element 18 at peripheral surface 28, which extends around the periphery of posterior element 20 and is a flat surface. Elements 18 and 20 can be secured together using known biocompatible adhesives. Anterior element 18 and posterior element 20 can also be formed from one material to eliminate the need to secure two elements together. In some embodiments the diameter of the region at which anterior element 18 and posterior element 20 are secured to one another is about 5.4 mm to about 6 mm in diameter.

In some embodiments the thickness of anterior element 18 (measured in the anterior-to-posterior direction) is greater along the optical axis ("OA" in FIG. 1C) than at the periphery. In some embodiments the thickness increases continuously from the periphery towards the thickest portion along the optical axis.

In some embodiments the thickness of posterior element 20 decreases from the location along the optical axis towards the edge of central region "CR" identified in FIG. 1C. The thickness increases again radially outward of central region CR towards the periphery, as can be seen in FIG. 1C. In some particular embodiments central region CR is about 3.75 mm in diameter. The apertures are formed in beveled surface 30.

In some embodiments the thickness of posterior element 20 along the optical axis is between about 0.45 mm and about 0.55 mm and the thickness at the periphery of posterior element 20 is between about 1.0 mm and about 1.3.

In some embodiments the thickness of posterior element 20 along the optical axis is about 0.5 mm and the thickness at the periphery of posterior element 20 is about 1.14 mm.

In some embodiments the thickness of anterior element 18 along the optical axis is between about 0.45 mm to about 0.55 mm, and in some embodiments is between about 0.50 mm to about 0.52 mm. In some embodiments the thickness at the periphery of anterior element 18 is between about 0.15 mm and about 0.4 mm, and in some embodiments is between about 0.19 mm and about 0.38 mm.

In one particular embodiment the thickness of anterior element 18 along the optical axis is about 0.52 mm and the thickness of the periphery of anterior element 18 is about 0.38 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.5 mm and the thickness of the periphery of anterior element 18 is about 0.3 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.51 mm and the thickness of the periphery of anterior element 18 is about 0.24 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.52 mm and the thickness of the periphery of anterior element 18 is about 0.19 mm, and the thickness of posterior element 20 along the optical axis is about 0.5 mm and the thickness at the periphery of posterior element 20 is about 1.14 mm.

The optic portion is adapted to maintain optical quality throughout accommodation. This ensures that as the accommodating intraocular lens transitions between the dis-accommodated and accommodated configurations, the optic portion maintains optical quality. A number of factors contribute to this beneficial feature of the accommodating intraocular lenses herein. These factors include the peripheral region at which anterior element 18 is secured to posterior element 20, the shape profile of the anterior element 18 and posterior element 20 inside central region CR of the optic portion (see FIG. 1C), and the thickness profiles of anterior element 18 and posterior element 20. These contributing factors ensure that both the anterior and posterior elements flex in such a way as to maintain the shape necessary to maintain optical quality across a range of optical powers.

Figure 1F:
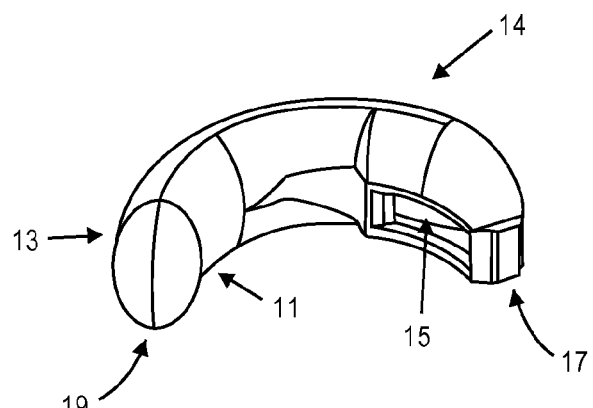
FIGS. 1F and 1G illustrate an exemplary haptic.

FIG. 1F illustrates one haptic 14 from intraocular lens 10 (optic portion 12 and the second haptic not shown for clarity). Haptic 14 includes radially outer portion 13 adapted to face the direction of the zonules, and radially inner portion 11, which faces the periphery of the optic (not shown). Haptic 14 includes a first end region 17 which is secured to optic portion 12, and second end region 19 that is closed. Haptic 14 also includes opening 15 in first end region 17 that provides the fluid communication with the haptic. In this embodiment opening 15 is sized and configured to receive buttress portion 29 of optic portion 12 therein.

Figure 1G:
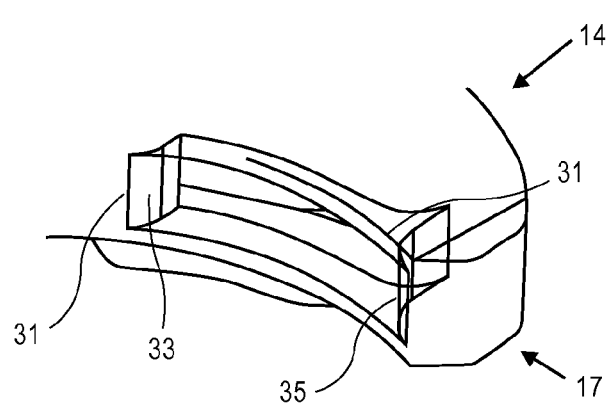

FIG. 1G is a close up view of opening 15 in haptic 14, which is adapted to receive buttress portion 29 therein. The opening 15 has curved surfaces 33 and 35 that are shaped to mate with curved surfaces on the optic buttress 29. Surface 31 surrounds opening 15 and provides a surface to which a corresponding surface of the optic can be secured.

Figure 1H:
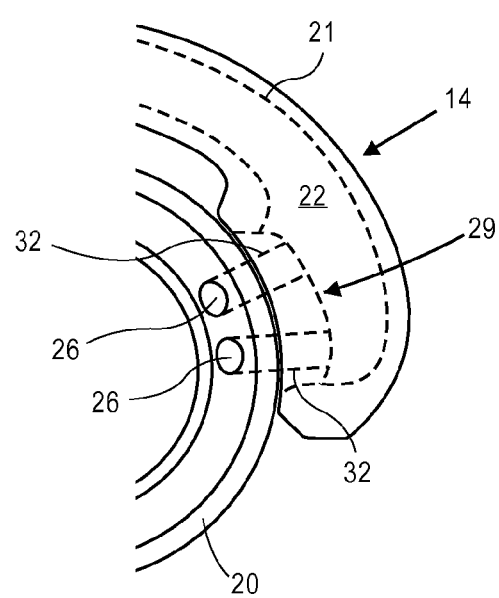
FIG. 1H illustrate an exemplary coupling between an optic portion and a haptic.

FIG. 1H is a top close up view of buttress portion 29 (in phantom) from posterior element 20 disposed within opening 15 in haptic 14 (anterior element of the optic not shown for clarity). Channels 32 are shown in phantom. Haptic 14 includes fluid chamber 22 defined by inner surface 21. Fluid moves between the optic fluid chamber and haptic fluid chamber 22 through channels 32 upon the deformation of haptic 14.

Figure 2A:
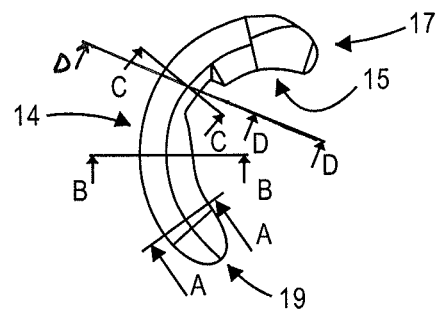
FIGS. 2A-2C illustrate an exemplary haptic.
Figure 2B:
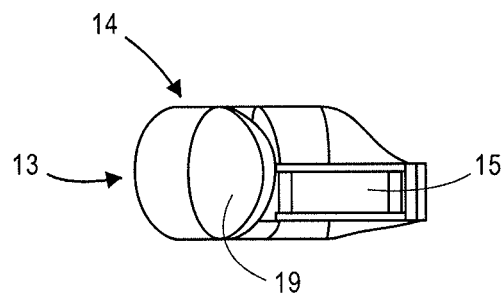
Figure 2C:
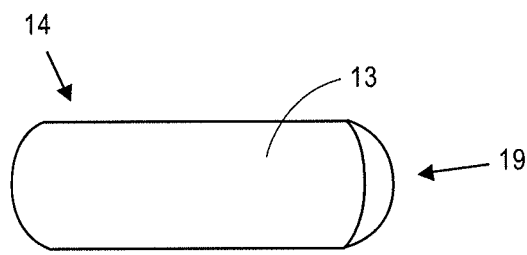

FIG. 2A is a top view showing one haptic 14 shown in FIGS. 1A-1H. The optic portion and the second haptic are not shown. Four sections A-D are identified through the haptic. FIG. 2B illustrates a side view of haptic 14, showing opening 15 and closed end 19. FIG. 2C is a side view of haptic 14 showing radially outer portion 13 and closed end 19.

Figure 2D:
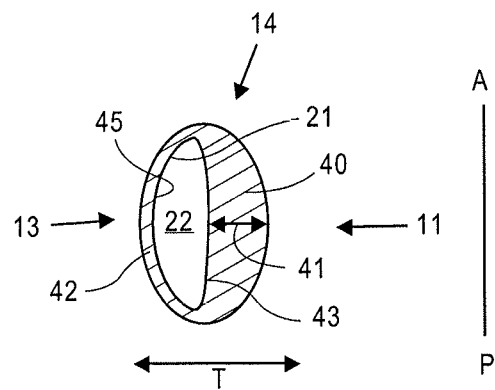
FIGS. 2D-2F illustrate sectional views of the haptic from FIG. 2A.

FIG. 2D is the cross sectional view through section A-A shown in FIG. 2A. Of the four sections shown in FIG. 2A, section A-A is the section closest to closed end 19. Radially inner portion 11 and radially outer portion 13 are identified. Fluid channel 22 defined by surface 21 is also shown. In this section the radially inner portion 40 is radially thicker (in the direction "T") than radially outer portion 42. Inner portion 40 provides the haptic's stiffness in the anterior-to-posterior direction that more predictably reshapes the capsule in the anterior-to-posterior direction. Radially inner portion 40 has a greatest thickness dimension 41, which is along an axis of symmetry in this cross section. The outer surface of haptic 14 has a generally elliptical configuration in which the greatest height dimension, in the anterior-to-posterior direction ("A-P"), is greater than the greatest thickness dimension (measured in the "T" dimension). The fluid chamber 22 has a general D-shaped configuration, in which the radially inner wall 43 is less curved (but not perfectly linear) than radial outer wall 45. Radially outer portion 42 engages the capsular bag where the zonules attach thereto, whereas the thicker radially inner portion 40 is disposed adjacent the optic.

Figure 2E:
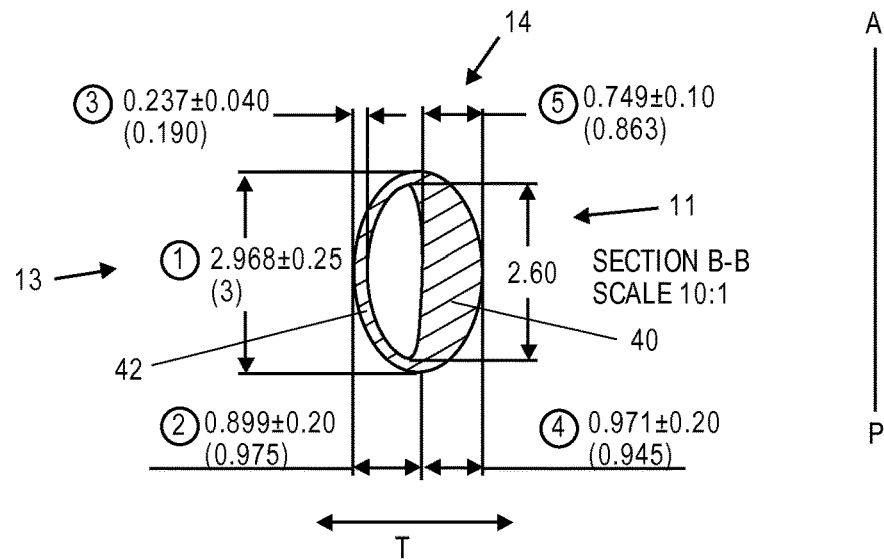

FIG. 2E illustrates section B-B shown in FIG. 2A. Section B-B is substantially the same as section A-A, and FIG. 2E provides exemplary dimensions for both sections. Radially inner portion 40 has a greatest thickness along the midline of about 0.75 mm (in the radial direction "T"). Radially outer portion 42 has a thickness along the midline of about 0.24 mm. Fluid chamber 22 has a thickness of about 0.88 mm. Haptic 14 has a thickness along the midline of about 1.87 mm. The height of the haptic in the anterior to posterior dimension is about 2.97 mm. The height of the fluid chamber is about 2.60 mm. In this embodiment the thickness of the radially inner portion 40 is about 3 times the thickness of the radially outer portion 42. In some embodiments the thickness of the radially inner portion 40 is about 2 times the thickness of the radially outer portion 42. In some embodiments the thickness of the radially inner portion 40 is about 2 to about 3 times the thickness of the radially outer portion 42. In some embodiments the thickness of the radially inner portion 40 is about 1 to about 2 times the thickness of the radially outer portion 42.

Fluid chamber 22 is disposed in the radially outer portion of haptic 14. Substantially the entire radially inner region of haptic 14 in this section is bulk material. Since the fluid chamber 22 is defined by surfaces 43 and 45 (see FIG. 2D), the positioning and size of fluid chamber 22 depends on the thickness of the radially inner portion 40 and the radially outer portion 42.

Figure 2F:
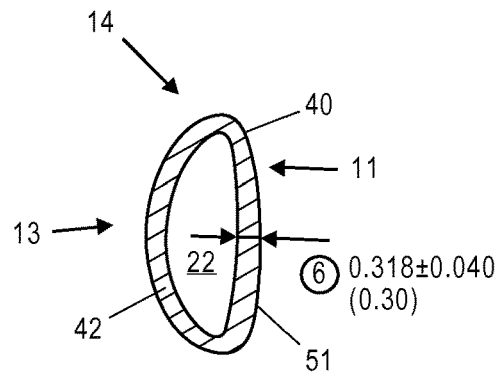

FIG. 2F illustrates Section C-C shown in FIG. 2A. In Section C-C radially inner portion 40 is not as thick as radially inner portion 40 in sections A-A and B-B, although in Section C-C radially inner portion 40 is slightly thicker than radially outer portion 42. In this particular embodiment radially inner portion 40 is about 0.32 mm in Section C-C. Radially outer portion 42 has a thickness about the same as the radially outer thickness in Sections A-A and B-B, about 0.24 mm. The outer surface of haptic 14 does not have the same configuration as the outer surface in Sections A-A and Section B-B. In Section C-C the radially inner surface of haptic 51 is more linear than in Sections A-A and Section B-B, giving the outer surface of haptic in Section C-C a general D-shape. In Section C-C fluid chamber 22 has a general D-shape, as in Sections A-A and Section B-B. The haptic, in Section C-C has a fluid chamber configuration that is substantially the same as the fluid chamber configurations in Sections A-A and B-B, but has an outer surface with a configuration different than the configuration of the outer surface of haptic 14 in Sections A-A and B-B.

The thinner radially inner portion 40 in Section C-C also creates access pathways 23 that are shown in FIG. 1A. This space between optic portion 12 and haptics 14 allows a physician to insert one or more irrigation and/or aspiration devices into space 23 during the procedure and apply suction to remove viscoelastic fluid that may be used in the delivery of the intraocular lens into the eye. The pathways 23 could also be anywhere along the length of the haptic, and there could be more than one pathway 23. This application incorporates by reference the disclosure in FIGS. 23 and 24, and the textual description thereof, from U.S. Pub. No. 2008/0306588, which include a plurality of pathways in the haptics.

Figure 2G:
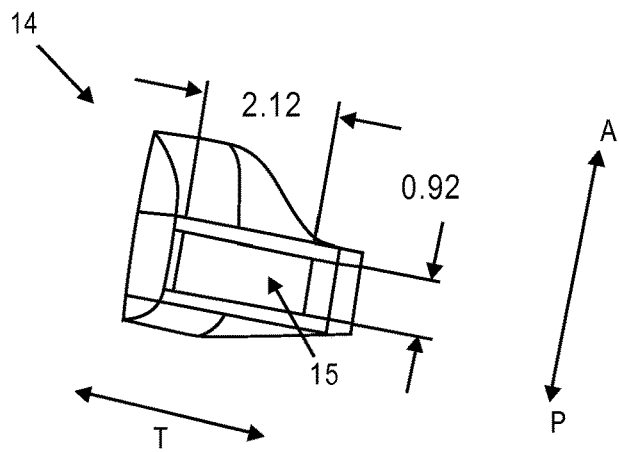
FIG. 2G illustrates an opening in a first end of the haptic from FIGS. 2A-2C.

FIG. 2G shows a partial sectional view through Section D-D from FIG. 2A. Haptic 14 includes opening 15 therein, which is adapted to receive the buttress from the optic portion as described herein. The height of opening 15 in this embodiment is about 0.92 mm. The width, or thickness, of the opening is about 2.12 mm.

Figure 3:
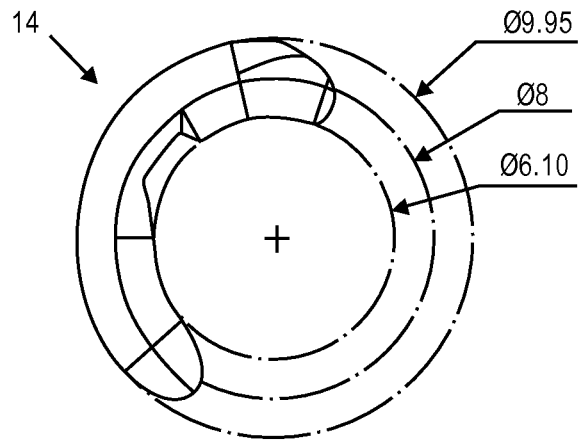
FIG. 3 illustrates exemplary diameters of an accommodating intraocular lens.

FIG. 3 illustrates relative diameters of optic portion 12 (not shown) and of the peripheral portion, which includes two haptics 14 (only one haptic is shown). In this embodiment the optic has a diameter of about 6.1 cm, while the entire accommodating intraocular lens, including the peripheral portion, has a diameter of about 9.95 cm. The dimensions provided are not intended to be strictly limiting.

Figure 4:
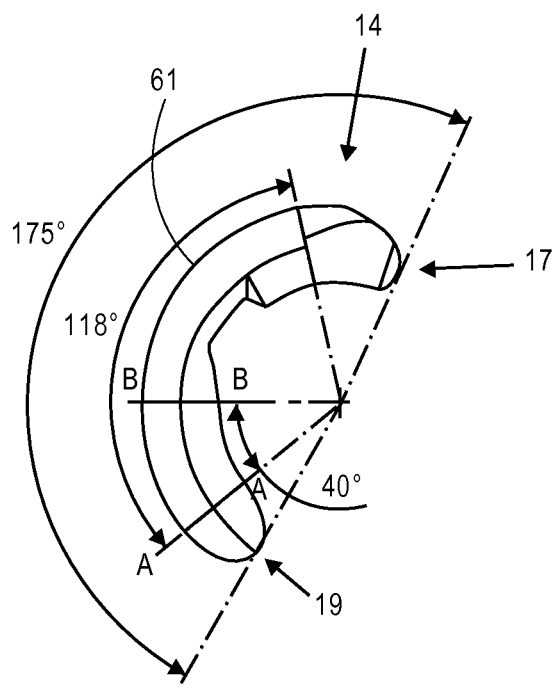
FIG. 4 illustrates an exemplary haptic.

FIG. 4 is a top view of haptic 14, showing that haptic 14 subtends an angle of about 175 degrees around optic (i.e., substantially 180 degrees). The optic portion is not shown for clarity. The two haptics therefore each subtend an angle of about 180 degrees around the optic. A first region 61 of haptic 14 is shown to subtend exemplary angle of about 118 degrees. This is the radially outermost portion of haptic 14, is adapted to engage the capsular bag, and is adapted to be most responsive to capsular shape changes. Region 61 can be thought of as the most responsive part of haptic 14.

The angle between Sections A-A and B-B, which are considered the boundaries of the stiffer radially inner portion of the haptic, is about 40 degrees. The stiff radially inner portion of haptic 14 is positioned directly adjacent the periphery of the optic. The dimensions and angles provided are not intended to be strictly limiting.

Figure 5A:
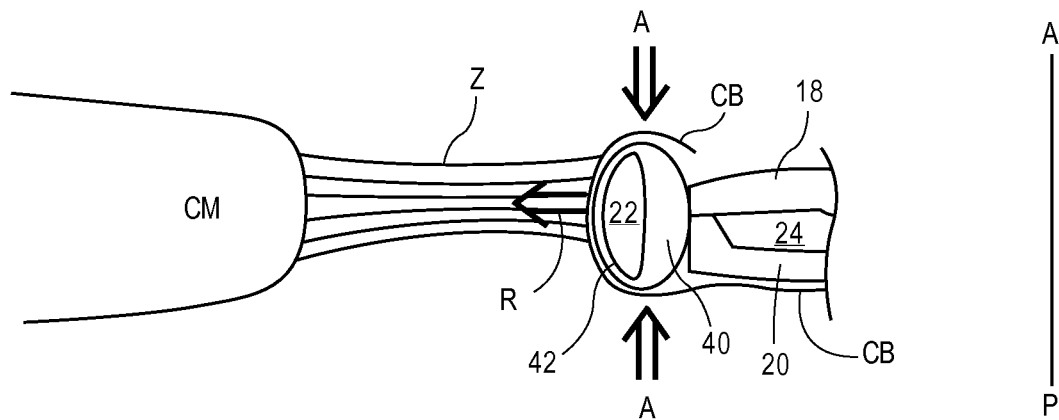
FIGS. 5A and 5B illustrate the deformation of an exemplary haptic in response to exemplary forces.
Figure 5B:
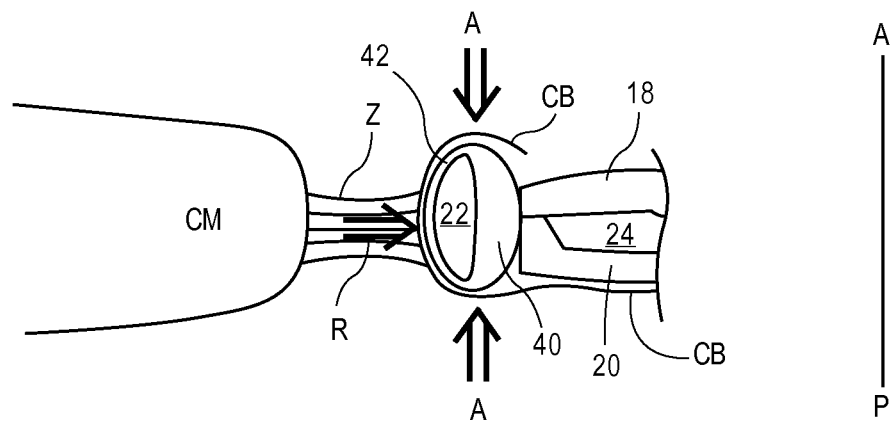

FIGS. 5A and 5B illustrate a portion of accommodating intraocular lens 10 positioned in a capsular bag ("CB") after a native lens has been removed from the CB. The anterior direction is on top and the posterior direction is on bottom in each figure. FIG. 5A shows the accommodating intraocular lens in a lower power, or dis-accommodated, configuration relative to the high power, or accommodated, configuration shown in FIG. 5B.

The elastic capsular bag "CB" is connected to zonules "Z," which are connected to ciliary muscles "CM." When the ciliary muscles relax, as shown in FIG. 5A, the zonules are stretched. This stretching pulls the capsular bag in the generally radially outward direction due to radially outward forces "R" due to the general equatorial connection location between the capsular bag and the zonules. The zonular stretching causes a general elongation and thinning of the capsular bag. When the native lens is still present in the capsular bag, the native lens becomes flatter (in the anterior-to-posterior direction) and taller in the radial direction, which gives the lens less power. Relaxation of the ciliary muscle, as shown in FIG. 5A, provides for distance vision.

When the ciliary muscles contract, however, as occurs when the eye is attempting to focus on near objects, the radially inner portion of the muscles move radially inward, causing the zonules to slacken. This is illustrated in FIG. 5B. The slack in the zonules allows the capsular bag to move towards a generally more curved configuration in which the anterior surface has greater curvature than in the disaccommodated configuration, providing higher power and allowing the eye to focus on near objects. This is generally referred to as "accommodation," and the lens is said to be in an "accommodated" configuration.

In section A-A (which is the same as section B-B) of haptic 14, illustrated in FIGS. 5A and 5B, radially inner portion 40 includes thicker bulk material that provides haptic 14 with stiffness in the anterior-to-posterior direction. When capsular bag forces are applied to the haptic in the anterior-to-posterior direction, the inner portion 40, due to its stiffness, deforms in a more repeatable and predictable manner making the base state of the lens more predictable. Additionally, the haptic, due to its stiffer inner portion, deforms the capsule in a repeatable way in the anterior-to-posterior direction. Additionally, because the haptic is less flexible along the length of the haptic, the accommodating intraocular lens's base state is more predictable because bending along the length of the haptic is one way in which fluid can be moved into the optic (and thereby changing the power of the lens). Additional advantages realized with the stiffer inner portion are that the haptics are stiffer to other forces such as torqueing and splaying because of the extra bulk in the inner portion.

The radially outer portion 42 is the portion of the haptic that directly engages the portion of the capsular bag that is connected to the zonules. Outer portion 42 of the haptics is adapted to respond to capsular reshaping forces "R" that are applied generally radially when the zonules relax and stretch. This allows the haptic to deform in response to ciliary muscle related forces (i.e., capsular contraction and relaxation) so that fluid will flow between the haptic and the optic in response to ciliary muscle relaxation and contraction. This is illustrated in FIG. 5B. When the ciliary muscles contract (FIG. 5B), the peripheral region of the elastic capsular bag reshapes and applies radially inward forces "R" on radially outer portion 42 of haptic 14. The radially outer portion 42 is adapted to deform in response to this capsular reshaping. The deformation decreases the volume of fluid channel 22, which forces fluid from haptic chamber 22 into optic chamber 24. This increases the fluid pressure in optic chamber 42. The increase in fluid pressure causes flexible anterior element 18 and flexible posterior element 20 to deform, increasing in curvature, and thus increasing the power of the intraocular lens.

The haptic is adapted to be stiffer in the anterior-to-posterior direction than in the radial direction. In this embodiment the radially outer portion 42 of haptic 14 is more flexible (i.e., less stiff) in the radial direction than the stiffer inner portion 40 is in the anterior-to-posterior direction. This is due to the relative thicknesses of outer portion 42 and inner portion 40. The haptic is thus adapted to deform less in response to forces in the anterior-to-posterior direction than to forces in the radial direction. This also causes less fluid to be moved from the haptic into the optic in response to forces in the anterior-to-posterior direction than is moved into the optic in response to forces in the radial direction. The haptic will also deform in a more predictable and repeatable manner due to its stiffer radially inner portion.

The peripheral portion is thus more sensitive to capsular bag reshaping in the radial direction than to capsular bag reshaping in the anterior-to-posterior direction. The haptics are adapted to deform to a greater extent radially than they are in the anterior-to-posterior direction. The disclosure herein therefore includes a peripheral portion that is less sensitive to capsular forces along a first axis, but is more sensitive to forces along a second axis. In the example above, the peripheral portion is less sensitive along the posterior-to-anterior axis, and is more sensitive in the radial axis.

An exemplary benefit of the peripheral portions described above is that they deform the capsular bag in a repeatable way and yet maintain a high degree of sensitivity to radial forces during accommodation. The peripheral portions described above are stiffer in the anterior-to-posterior direction than in the radial direction.

An additional example of capsular forces in the anterior-to-posterior direction is capsular forces on the peripheral portion after the accommodating intraocular lens is positioned in the capsular bag, and after the capsular bag generally undergoes a healing response. The healing response generally causes contraction forces on the haptic in the anterior-to-posterior direction, identified in FIG. 5A by forces "A." These and other post-implant, such as non-accommodating-related, capsular bag reshaping forces are described in U.S. application Ser. No. 12/685,531, filed Jan. 11, 2010, which is incorporated herein by reference. For example, there is some patient to patient variation in capsular bag size, as is also described in detail in U.S. application Ser. No. 12/685,531, filed Jan. 11, 2010. When an intraocular lens is positioned within a capsular bag, size differences between the capsule and intraocular lens may cause forces to be exerted on one or more portions of the intraocular lens in the anterior-to-posterior direction.

In the example of capsular healing forces in the anterior-to-posterior direction, the forces may be able to deform a deformable haptic before any accommodation occurs. This deformation changes the volume of the haptic fluid chamber, causing fluid to flow between the optic fluid chamber and the haptic fluid chambers. This can, in some instances undesirably, shift the base power of the lens. For example, fluid can be forced into the optic upon capsular healing, increasing the power of the accommodating intraocular lens, and creating a permanent myopic shift for the accommodating intraocular lens. Fluid could also be forced out of the optic and into the haptics, decreasing the power of the accommodating intraocular lens.

As used herein, "radial" need not be limited to exactly orthogonal to the anterior-to-posterior plane, but includes planes that are 45 degrees from the anterior-to-posterior plane.

Exemplary fluids are described in U.S. application Ser. No. 12/685,531, filed Jan. 11, 2010, and in U.S. application Ser. No. 13/033,474, filed Feb. 23, 2011, both of which are incorporated herein by reference. For example, the fluid can be a silicone oil that is or is not index-matched with the polymeric materials of the anterior and posterior elements. When using a fluid that is index matched with the bulk material of the optic portion, the entire optic portion acts a single lens whose outer curvature changes with increases and decreases in fluid pressure in the optic portion.

In the embodiment in FIGS. 2A-2G above the haptic is a deformable polymeric material that has a substantially uniform composition in Sections A-A, B-B, and C-C. The stiffer radially inner body portion 40 is attributed to its thickness. In alternative embodiments the radially inner body portion has a different composition that the outer body portion, wherein the radially inner body portion material is stiffer than the material of the radially outer body portion. In these alternative embodiments the thicknesses of the radially inner and outer portions can be the same.

Figure 6:
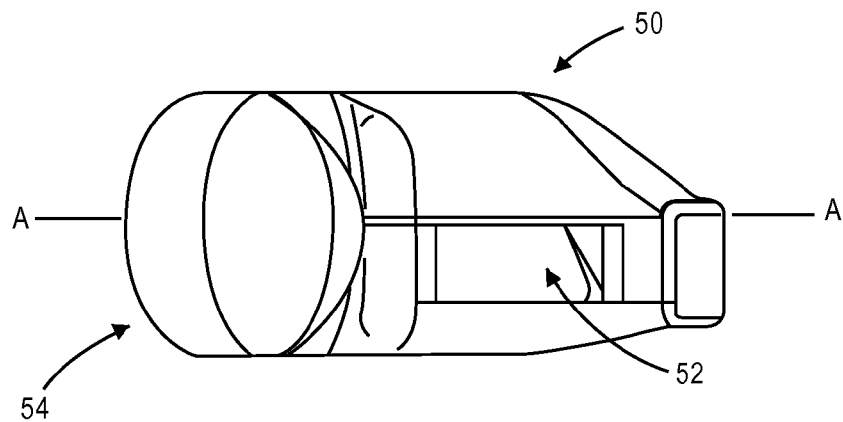
FIG. 6 illustrates an exemplary fluid opening in an exemplary haptic.

FIG. 6 illustrates haptic 50, which is the same haptic configuration as in shown in FIG. 2B. The radially outer portion 54 is identified. The haptic has axis A-A halfway through the height of the haptic. Opening 52, in which the optic buttress is disposed, is on the posterior side of axis A. In this embodiment the optic sits slightly closer to the posterior-most portion of the haptics than the anterior-most portion of the haptics.

Figure 7:
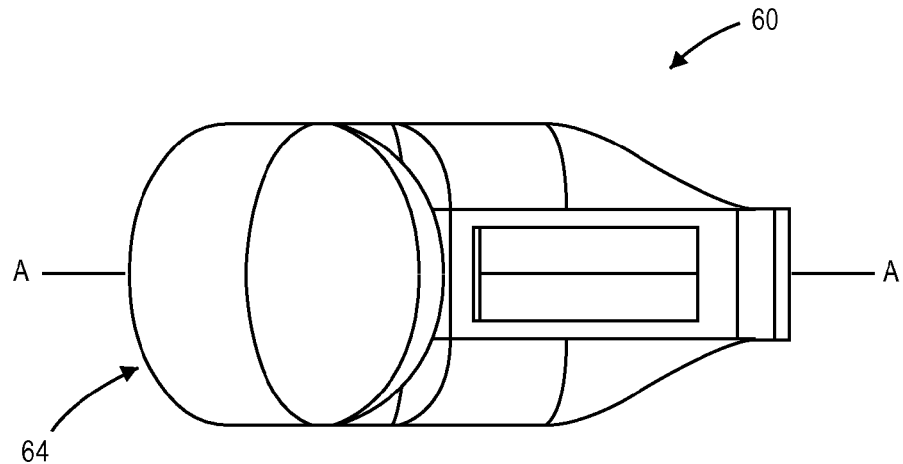
FIG. 7 illustrates an exemplary fluid opening in an exemplary haptic.
Figure 8:
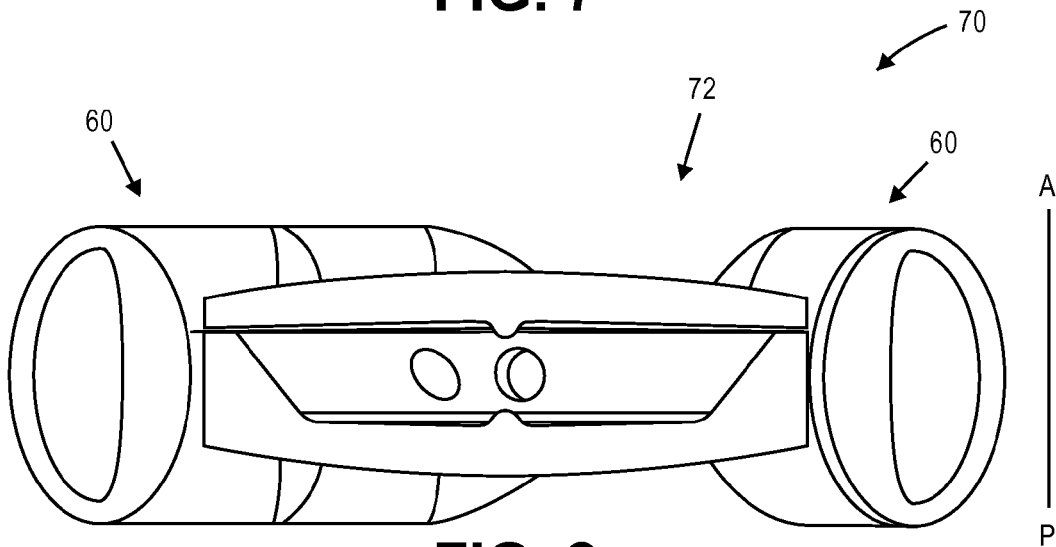
FIG. 8 illustrates a sectional view of an exemplary accommodating intraocular lens.

FIG. 7 illustrates an alternative haptic 60 (optic not shown), wherein the radially outer portion 64 is identified. Haptic 60 includes axis A-A halfway through the thickness of the haptic. Opening 62 is symmetrical about the axis A. Additionally, axis A-A is an axis of symmetry for haptic 60. The symmetry of the haptic along axis A can improve the ability to mold low relatively low stress components. FIG. 8 shows an embodiment of intraocular lens 70 in which the optic 72 is coupled to two haptics 60, which are the haptics shown in FIG. 7. The optic sits further in the anterior direction than in the embodiment in which the opening is not along the midline of the haptic. The cross sections A-A, B-B, and C-C of haptic 60 are the same as those shown in other embodiments shown above.

Figure 9:
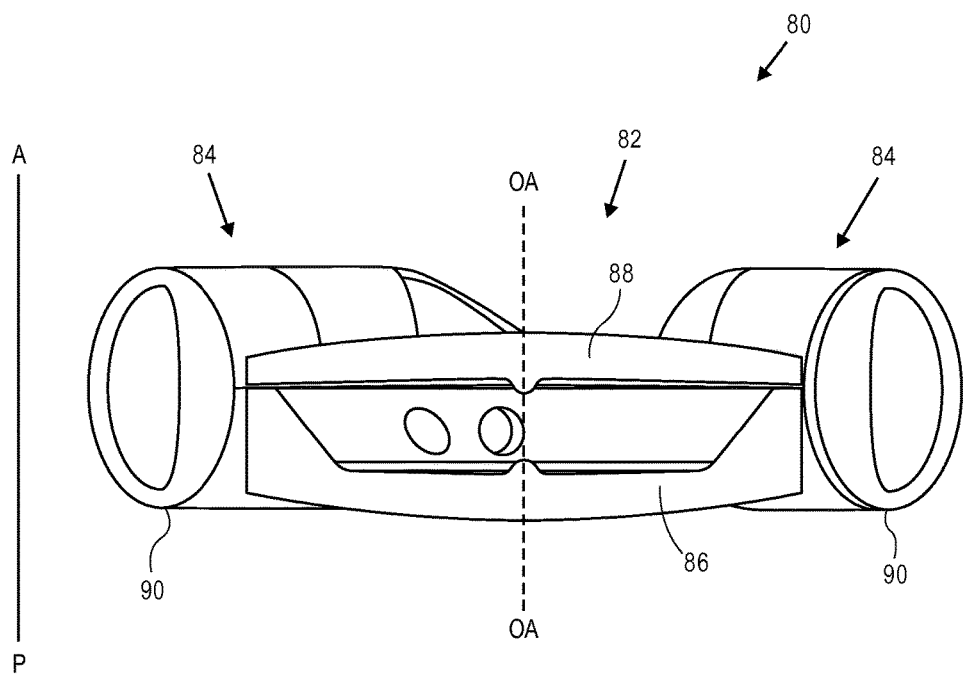
FIG. 9 illustrates a sectional view of an exemplary accommodating intraocular lens with relatively short haptics.

FIG. 9 illustrates intraocular lens 80 including optic 82 and two haptics 84. The optic is the same as the optic portions described herein. Haptics 84 are not as tall, measured in the anterior-to-posterior direction, as haptic 60, haptic 50, or haptic 14. In exemplary embodiments haptics 84 are between about 2.0 mm and about 3.5 mm tall, and in some embodiments they are about 2.8 mm tall. Intraocular lens 80 can be considered a size "small" accommodating intraocular lens for patients with a capsular bag that is below a certain threshold size. The posterior surface of posterior element 86 is disposed slightly further in the posterior direction than the posterior-most portions 90 of haptics 84.

Characteristics of the intraocular lenses described herein can similarly be applied to non-fluid driven accommodating intraocular lenses. For example, a non-accommodating intraocular lens can include a peripheral portion with a first stiffer region that provides a region of the peripheral portion with an insensitivity in a first direction. For example, in an intraocular lens with two lenses adapted to be moved apart from one another to change the power of the lens, the peripheral portion of the lens can be adapted such that a first type of capsular reshaping does not cause the distance between the lenses to change, and thus the power of the intraocular lens stays the same.

Additionally, the accommodating intraocular lenses herein can also be adapted to be positioned outside of a native capsular bag. For example, the accommodating intraocular lenses can be adapted to be positioned in front of, or anterior to, the capsular bag after the native lens has been removed or while the native lens is still in the capsular bag, wherein the peripheral portion of the lens is adapted to respond directly with ciliary muscle rather than rely on capsular reshaping.

What is claimed is:

1. An accommodating intraocular lens, comprising:
an optic portion comprising an optical axis and an optic fluid chamber; and
a haptic having a proximal portion secured to the optic portion and a free distal portion disposed away from the proximal portion, wherein a radially innermost surface of the haptic, relative to the optical axis, from the proximal portion to the free distal portion, follows a curved radially-outer peripheral surface of the optic portion, and
in a first cross section between the proximal portion and the free distal portion, the haptic has a first radially innermost wall radial thickness and a radially outermost wall thickness, the radial thicknesses measured orthogonal to the optical axis, and the radially innermost surface is directly adjacent the optic portion, the first inner wall radial thickness being greater than the radially outermost wall thickness, wherein the thicker inner wall radial thickness adapts the haptic to be more sensitive to capsular forces in the radial direction than to capsular forces in the anterior-to-posterior direction, and
in a second cross section closer to the proximal portion than the first cross section, the haptic has a second radially innermost wall radial thickness less than the first radially innermost wall radial thickness and the radially innermost surface is radially further from the optic portion than in the first cross section, the haptic comprising a haptic fluid chamber in fluid communication with the optic fluid chamber,
wherein in each of the first and second cross sections there is only a single lumen, the single lumen being the haptic fluid chamber,
wherein the haptic fluid chamber has the same configuration, in cross section, in the first section and the second section,
wherein the haptic is adapted to deform in response to forces on the haptic due to ciliary muscle movement to thereby move a fluid between the haptic fluid chamber and the optic fluid chamber to change an optical parameter of the accommodating intraocular lens.

2. The accommodating intraocular lens of claim 1 wherein the haptic is adapted to be more sensitive to capsular bag forces in the radial direction than it is to capsular bag forces in the anterior-to-posterior direction.

3. The accommodating intraocular lens of claim 1 wherein the haptic is adapted to deform more in response to forces in the radial direction that it is to forces in the anterior-to-posterior direction.

4. The accommodating intraocular lens of claim 1 wherein the haptic is adapted such that a greater volume of fluid moves between the peripheral fluid chamber and the optic fluid chamber in response to forces on the haptic in the radial direction that in response to forces on the haptic in the anterior-to-posterior direction.

5. The accommodating intraocular lens of claim 1 wherein the first inner wall radial thickness is about three times the thickness of the outer wall radial thickness along a midline of the haptic.

6. The accommodating intraocular lens of claim 1, wherein in the first cross section the haptic fluid chamber has a radially inner surface that is more linear than a haptic fluid chamber radially outer surface.

7. The accommodating intraocular lens of claim 1, wherein the haptic has a first portion that includes the first cross section with the first radially innermost wall thickness, and wherein the first radially innermost wall thickness subtends an angle of about 40 degrees around the optic portion.

* * * * *